(12) United States Patent  (10) Patent No.: US 8,710,431 B2
Newton  (45) Date of Patent: Apr. 29, 2014

(54) DUAL SOURCE MASS SPECTROMETRY SYSTEM

(75) Inventor: Anthony Newton, Cheshire (GB)

(73) Assignee: Micromass UK Limited, Manchester (GB)

( * ) Notice: Subject to any disclaimer, the term of this patent is extended or adjusted under 35 U.S.C. 154(b) by 146 days.

(21) Appl. No.: 13/202,641

(22) PCT Filed: Mar. 8, 2010

(86) PCT No.: PCT/GB2010/050391
§ 371 (c)(1),
(2), (4) Date: Oct. 26, 2011

(87) PCT Pub. No.: WO2010/100507
PCT Pub. Date: Sep. 10, 2010

(65) Prior Publication Data
US 2012/0126108 A1  May 24, 2012

Related U.S. Application Data

(60) Provisional application No. 61/184,915, filed on Jun. 8, 2009.

(30) Foreign Application Priority Data

Mar. 6, 2009  (GB) .................................. 0903908.2

(51) Int. Cl.
*B01D 59/44*  (2006.01)
*H01J 49/00*  (2006.01)

(52) U.S. Cl.
USPC ............................ 250/288; 250/281; 250/282

(58) Field of Classification Search
USPC ........................... 250/288, 282, 423 R, 323 R
See application file for complete search history.

(56) References Cited

U.S. PATENT DOCUMENTS 6,646,257 B1  11/2003  Fischer et al.
2008/0048107 A1*  2/2008  Mcewen ........................ 250/282
(Continued)

FOREIGN PATENT DOCUMENTS

JP  2004130263  1/1992
JP  2006215729  5/1994
(Continued)

OTHER PUBLICATIONS

International Search Report for application No. PCT/GB2010/050391, mailing date of Jul. 6, 2010, 7 pages.
(Continued)

*Primary Examiner* — Nikita Wells
*Assistant Examiner* — Johnnie L Smith
(74) *Attorney, Agent, or Firm* — Waters Technologies Corp.

(57) ABSTRACT

A dual source mass spectrometer system (10) is operable in a first mode with an LC source [LC/MS] (12) and in a second mode with a GC source [GC/MS] (18). The GC source inputs into an ion source chamber (22) for delivering the ionized output from the GC source to the mass spectrometer. The GC source comprises a GC interface probe (30) which is retractably connected to the ion source chamber to take the GC interface probe from a retracted position in which it is disengaged from the mass spectrometer (whereby the system is operable in the first LC/MS mode) into a deployed position in which the GC interface probe is operatively connected to the ion source chamber of the mass spectrometer (whereby the system is operable in said second GC/MS mode).

7 Claims, 8 Drawing Sheets

(56) References Cited

U.S. PATENT DOCUMENTS

| | | | |
|---|---|---|---|
| 2008/0296485 A1 | 12/2008 | Benter et al. | |
| 2012/0097844 A1* | 4/2012 | Newton | 250/288 |
| 2012/0104246 A1* | 5/2012 | Newton | 250/288 |
| 2012/0126108 A1* | 5/2012 | Newton | 250/282 |

FOREIGN PATENT DOCUMENTS

| | | |
|---|---|---|
| JP | 2004342620 | 2/2004 |
| WO | 2009137463 | 11/2009 |

OTHER PUBLICATIONS

International Written Report for application No. PCT/GB2010/050391, mailing date of Jul. 6, 2010, 8 pages.

International Search Report for application No. PCT/GB2010/050392, mailing date of Jul. 6, 2010, 7 pages.

International Written Report for application No. PCT/GB2010/050392, mailing date of Jul. 6, 2010, 8 pages.

International Search Report for application No. PCT/GB2010/050393, mailing date of Jul. 6, 2010, 7 pages.

International Written Report for application No. PCT/GB2010/050393, mailing date of Jul. 6, 2010, 8 pages.

JEOL Ltd; Interruption Control Method and Circuit for Analysis Apparatus, Journal of Technical Disclosure No. 2004-500966, Publication Date: Feb. 18, 2004, pp. 4.

Translation of Notice of Rejection (Official Action), for Japanese Patent Application No. 2011-552530, Mailing Date: Jan. 28, 2014, pp. 2.

\* cited by examiner

DUAL SOURCE MASS SPECTROMETRY SYSTEM

BACKGROUND OF THE INVENTION

1. Field of the Invention

The present invention is directed generally to scientific laboratory analytical equipment, and more particularly, to the combination of Chromatography Systems and Mass Spectrometers.

2. Background of the Related Art

Scientific laboratories commonly need to analyse samples by the use of Chromatography in order to separate different constituents within the samples. Once the samples have been separated, they may need further analysis in order to identify what the different constituents are. Normally the most effective way of performing the analysis of the separated constituents is the use of mass spectrometers.

Chromatography can be performed either on gaseous samples or on liquid samples. However, the apparatus required to perform Liquid Chromatography and Gas Chromatography are rather different, so much so that different machines are required to perform the different analyses.

Mass spectrometers can be used to measure the mass of ions and analyse the structure of these ions, by studying fragmentation of the ions that may occur within the mass spectrometer. Chromatography systems typically produce molecules rather than ions, so the mass spectrometer needs to produce ions from the molecules that are delivered to it. This typically is performed in an ion source. There are many ways of ionizing the molecules that are injected into an ion source. Atmospheric Pressure Chemical Ionisation [APCI] is one of these methods. In this method, the molecules are sprayed into an ion source chamber and the spray is subjected to a corona discharge that creates ions.

APCI is a desirable fragmentation technique because it typically produces singly charged ions, and so the results of the analysis are easier to interpret. Furthermore APCI is a method of ionization that is possible to use for samples that are both liquid and gaseous.

Mass Spectrometers are complicated and precise instruments, and so are expensive and delicate. Until recently, they have always been specifically designed for one of LCMS or GCMS and not for interchangeable use. In the past also instruments have been designed to swap between GCMS and LCMS. However, the changeover has been time consuming and often the dual instruments compromised the performance on one or the other of the two techniques. This is especially true for Vacuum GCMS systems utilizing Electron Impact Ionization. The advantage of using APCI is that both LCMS and GCMS are operated at the same pressure and there is no need to change the MS other than to put an ion chamber on in place of a cone gas nozzle.

An attempt to provide a dual source mass spectrometry system comprises a mass spectrometer that has an ion source capable of being used for either LCMS or GCMS. However the design of the source is such that both an LCMS interface probe and a GCMS interface probe are permanently connected to an API source housing. This arrangement is an improvement over the use of separate LCMS and GCMS machines but is inefficient, and so cannot easily identify small quantities of analytes that may be present in the sample.

It would therefore be desirable to produce a Mass Spectrometer that is capable of efficiently analysing the output of either liquid or gas chromatography systems with easy transfer between the two different inputs, and with easy and minimal alterations required as now provided by the present invention.

It is envisaged that the dual source mass spectrometry system of the present invention has applications for example in synthetics confirmation and impurity profiling, natural products research, and in the fields of flavours and fragrances, nutraceuticals, petrochemicals, metabolomics, environmental screening, pesticide residue analysis and some forensic applications. The combination of LCMS and GCMS allows a wider range of compounds to be analyzed on a single instrument platform.

SUMMARY OF THE INVENTION

One aspect of the present invention provides a dual source mass spectrometer system operable in a first mode with an LC source [LC/MS] and in a second mode with a GC source [GC/MS], said GC source inputting into an ion source chamber for delivering the ionized output from the GC source to the mass spectrometer and wherein the GC source comprises a GC interface probe which is retractably connected to said ion source chamber to take the GC interface probe from a retracted position in which it is disengaged from the mass spectrometer, whereby the system is operable in said first LC/MS mode, into a deployed position in which the GC interface probe is operatively connected to the ion source chamber of the mass spectrometer whereby the system is operable in said second GC/MS mode. In LCMS mode the ion chamber is not used. It is replaced with a cone gas nozzle and the corona discharge is carried out in the source enclosure on the eluent from the APCI probe.

According to a feature of the invention the GC interface probe and a housing of the ion source chamber may have complementary docking means so that they can be releasably engaged to allow operation with a GC ion source chamber in said second mode. Preferably, the docking means comprises a docking port in the GC ion source housing to receive the GC interface probe and complementary locking means by which the probe can be progressively drawn into the docking port and releasably locked in position. The GC interface probe docks on the ion source housing such that the end of the transfer line positions in the back of the chamber which is open. It is also preferred that the docking port comprises a screw-threaded nozzle incorporating sealing means and the GC interface probe comprises a complementary screw-threaded locking lever to releasably engage the nozzle whereby the probe can be sealingly coupled with the nozzle.

According to another feature of the invention the GC interface probe may be carried by a gas chromatography unit which is retractably connectable to a mass spectrometer of the system when a GC ion source chamber is present. Preferably, the gas chromatography unit is slidably connectable to the mass spectrometer of the system. It is further a preferred feature that the gas chromatography unit incorporates a lockable rail system to allow slidable movement of the unit over the rail system so that it can be offered up to, and retracted from, the mass spectrometer of the system.

Another aspect of the invention provides a method of operating a dual source mass spectrometer system in a first mode with an LC source [LC/MS] and in a second mode with a GC source [GC/MS], said GC source inputting into an ion source chamber for delivering the ionized output from the GC source to the mass spectrometer and wherein the GC source comprises a GC interface probe, the method comprising the steps of taking the GC interface probe from a retracted position in which it is disengaged from the ion source chamber, whereby the system is operable in said first LC/MS mode, into a deployed position in which the GC interface probe is operatively connected to the ion source chamber whereby the system is operable in said second GC/MS mode.

According to another feature of this aspect of the invention, complementary docking means provided between the GC interface probe and a housing of the ion source chamber may be actuated so that the probe and the housing can be releasably engaged to allow operation with a GC ion source chamber in said second mode and substitution of the GC ion source housing by an LC ion source housing to allow operation with the LC ion source chamber in said first mode. Preferably, the docking means comprises a docking port and the complementary locking means is actuated such that the probe is progressively drawn into the docking port and releasably locked in position. It is further preferred that the docking port comprises a screw-threaded nozzle incorporating sealing means and the GC interface probe comprises a complementary screw-threaded locking lever and wherein the locking lever is manipulated to releasably engage the nozzle whereby the probe can be sealingly coupled with the nozzle.

According to a still further feature of this aspect of the invention, the GC interface probe may be carried by a gas chromatography unit, and wherein the gas chromatography unit is retractably connected to a mass spectrometer of the system when a GC ion source chamber is present. Still more preferably, where this feature is adopted the gas chromatography unit is slidably connected to the mass spectrometer of the system. Even more preferably, the gas chromatography unit incorporates a lockable rail system the method comprising slidable movement of the unit over the rail system so that it is offered up to and retracted from the mass spectrometer of the system.

DESCRIPTION OF THE DRAWINGS

An embodiment of the invention will now be described, by way of example, with reference to the accompanying drawings, in which:—

SPECIFIC DESCRIPTION

Figure 1:
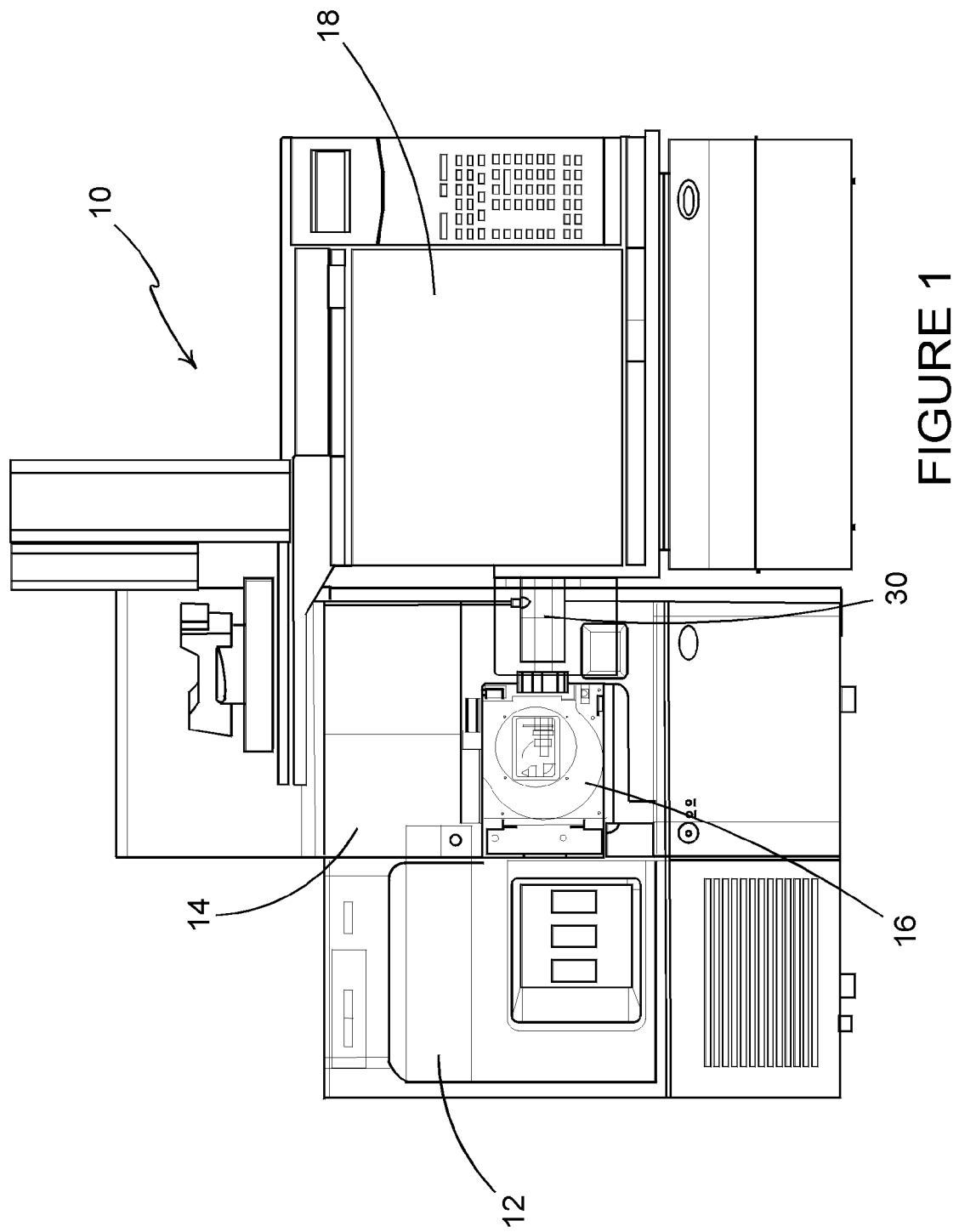
FIG. 1 is a perspective view of the dual source mass spectrometry system comprising an LC source unit, an MS unit and a GC unit.

Referring to the drawings there is shown a dual source mass spectrometry system 10 which comprises a liquid chromatography [LC] unit 12, a mass spectrometer [MS] unit 14, an ion source housing 16 which may be suitable for use with the LC unit or with the GC unit and a gas chromatography [GC] unit 18.

When it is required for the system to operate in LC/MS mode, the ion source housing 16 is one which is appropriate for use with a LC column of the LC unit 12 in which case the GC unit 18 is disengaged and refracted from the MS unit 14. In order to operate the system in GC/MS mode, the LC ion source housing (not shown) is substituted by a GC ion source housing and the GC unit 18 is put into a deployed position in which it is operatively connected to the MS unit.

Figure 2:
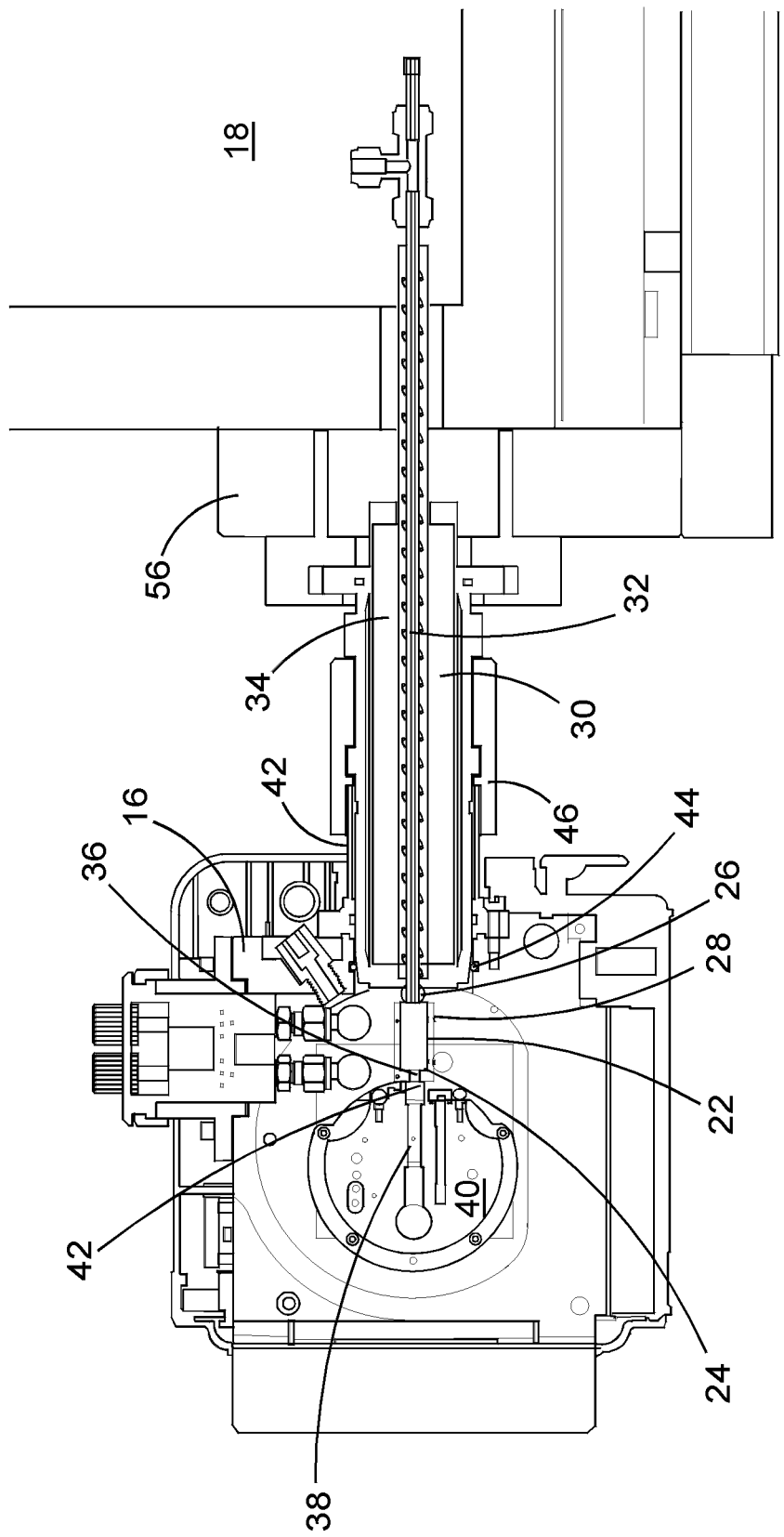
FIG. 2 is a cross-sectional view of the GC ion source housing and the GC interface probe.

Referring now to FIG. 2 of the drawings, the GC ion source housing 16 incorporates an ion source chamber 22. The chamber 22 has at least one outlet port 24, at least one gas inlet (not shown), a sample port 26, and at least one corona pin port 28.

The housing 16 is made of a structural material such as plastics, metal, glass or ceramic. A preferred metal is stainless steel, titanium, aluminium, copper, brass and other alloys.

The sample port 26 is constructed and arranged to receive a GC interface probe 30 comprising a gas chromatographic column 32. The column is surrounded by a heated sheath gas tube 34. The gas chromatographic column 32 is for placing the analyte molecules in the chamber 22. The analyte molecules are suspended or dissolved in gas. The column has a mobile phase and a stationary phase and is used to separate components based upon their vapour pressure. When compounds elute from the column into the chamber they are in the vapour phase. Gas chromatographic columns are known in the art and are available from several venders. For example, without limitation, gas chromatographic columns are sold by Varian, Inc. (Palo Alto, Calif., USA) under several trademarks including FactorFour™, CP-Sil, and Select™

Figure 2A:
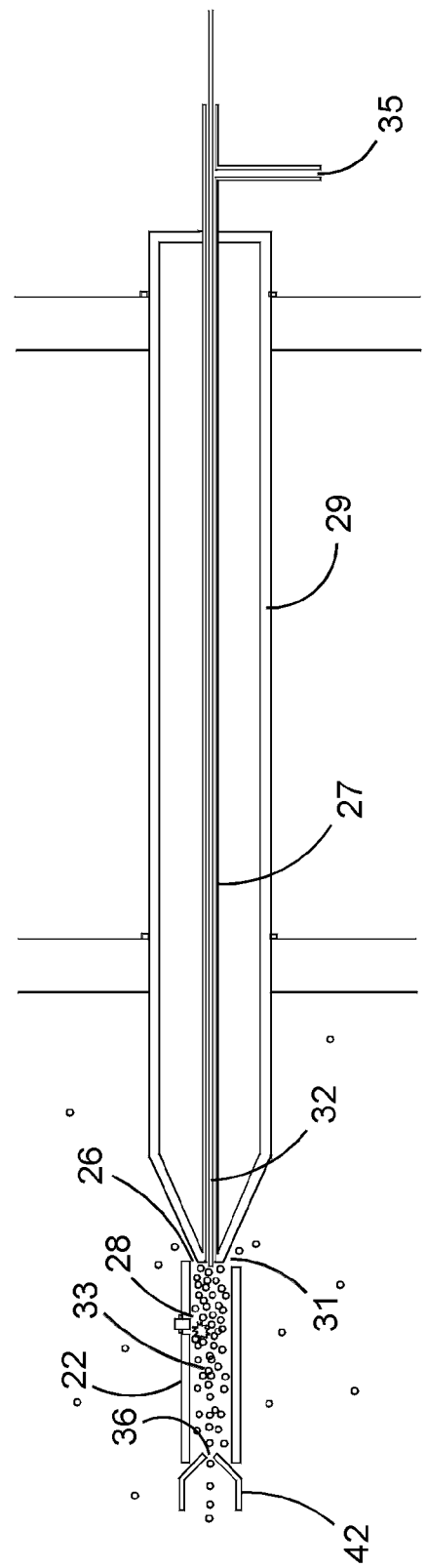
FIG. 2A is a schematic view of the GC transfer line showing the ion source enclosure or housing and the GC oven in the GC unit.

Referring to FIG. 2A, the sample port 26 receives the inner tube 27 of a transfer line 29 and transfer line tip 31 from which the column 32 protrudes. It is not a close fit but has a reasonable clearance with the transfer line to prevent the chamber from grounding on the metal transfer line. The outside wall of the column 32 and the inner diameter of the sample port cooperate to form a close fit. However, the fit need not be airtight. A gap allows excess gas in chamber 22 to vent and be carried off by a vent structure of the atmospheric pressure ionization housing. Thereby the chamber is swept out in the timescale of a chromatographic peak.

The gas inlet is constructed and arranged to be placed in fluid communication with a source of an inert gas [not shown] for placing the inert gas into the chamber 22. Inert gases comprise any substantially non-reactive gas, such as nitrogen. Such gases are sold by numerous venders under pressure in tanks.

The outlet port 24 is constructed and arranged to be received on or about an opening 36 of a vacuum region 38 of a mass spectrometer generally designated by the numeral 40. The opening 36 normally interfaces between the vacuum region 38 and an atmospheric pressure region of the atmospheric pressure ionization housing 16. The atmospheric region may deviate slightly from atmospheric but is substantially near atmospheric pressure.

Opening 36 is formed in an inlet cone 42 which substantially fills the outlet port 24 to form a substantially closed chamber 22. The chamber 22 has a volume of 0.5 to 5.0 cc when the outlet port 24 is received on or about the opening 36 of the vacuum region 38.

The opening 36 of the vacuum region 38 defines a sample axis. A preferred sample port 24 is constructed and arranged to introduce analyte molecules 33 within sixty degrees of a line perpendicular to the sample axis.

The corona pin port 28 is constructed and arranged for receiving a corona discharge pin for discharging electrons. The discharged electrons place a charge on analyte molecules 33 (FIG. 2) as the analyte molecules leave the gas chromatographic column 32. These charged and uncharged analyte molecules are circulated around the chamber 22 by the gas introduced through the gas inlet and received in the opening 36 of the vacuum region for mass analysis.

Preferably, the corona discharge port is constructed and arranged to place the corona discharge pin within the flow of the sample discharged from the gas chromatographic column 32. Usually, the corona discharge port is aligned with the sample axis allowing gases to circulate around the corona discharge pin. Plasma formed by corona discharge into a gas consists of the carrier gas in combination with make-up gas supplied through the transfer inner tube 27 through a connecting line 35.

In the case of N2 make-up gas $N2^+$ and $N4^+$ are formed in the plasma then $$N2^+ + M > M^+ + N2$$

$$N4^+ + M > M^+ + 2N2$$

In addition with trace amounts of moisture $H30^+$, then $$H30^+ + M > MH^+ + H20$$

With higher concentrations of water $H^+ (H20)_n$, then $$H^+(H20)_n + M > MH^+ + nH20$$

Selective ionization can also be performed by photo-ionization.

The removal of the GC ion source housing 16 allows the mass spectrometer to receive liquid samples from an LC atmospheric pressure ionization source [not shown] in a conventional manner.

Figure 3:
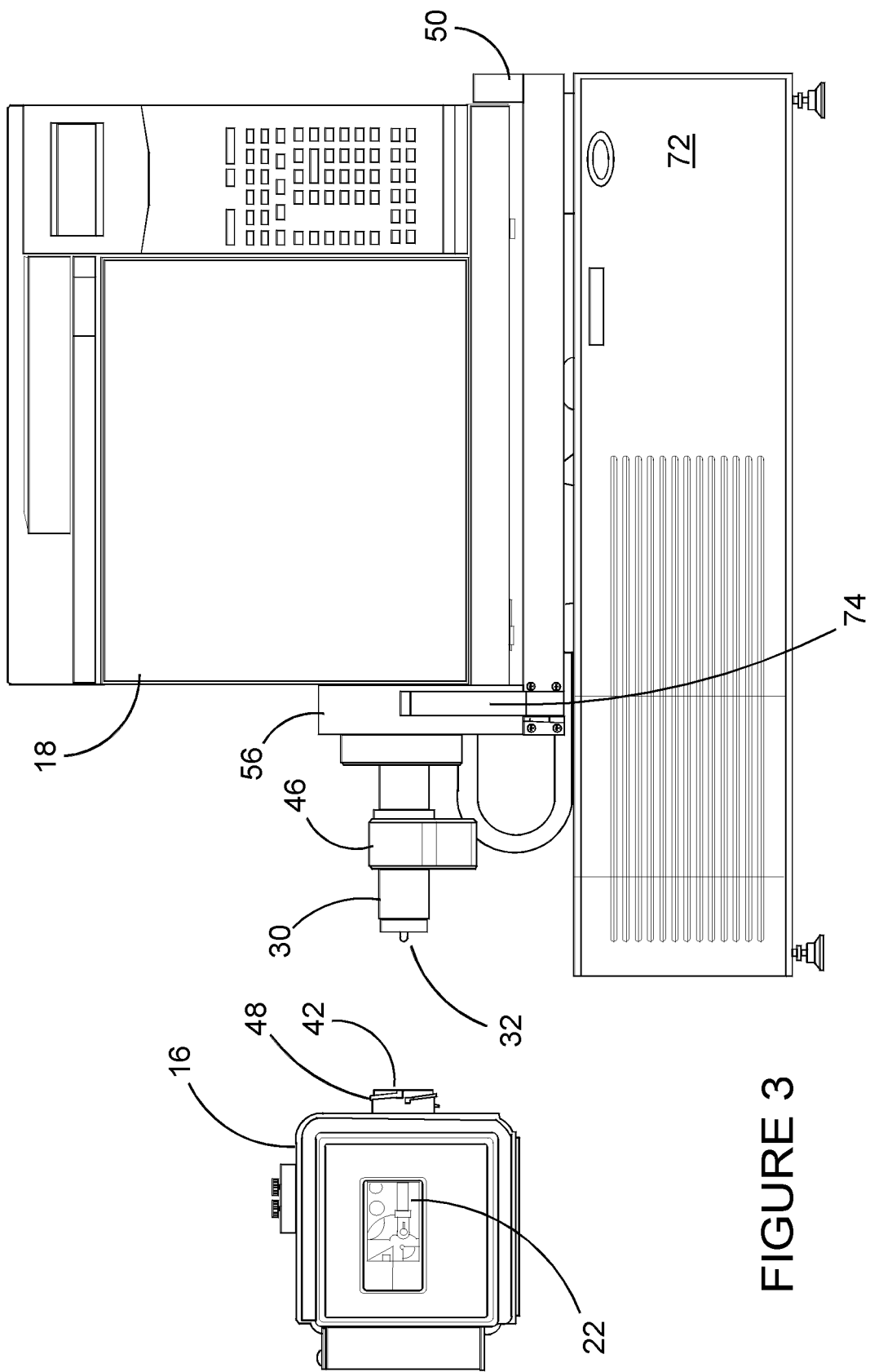
FIG. 3 is a perspective view of the GC unit and the GC ion source housing with the GC interface probe in a refracted position.
Figure 4:
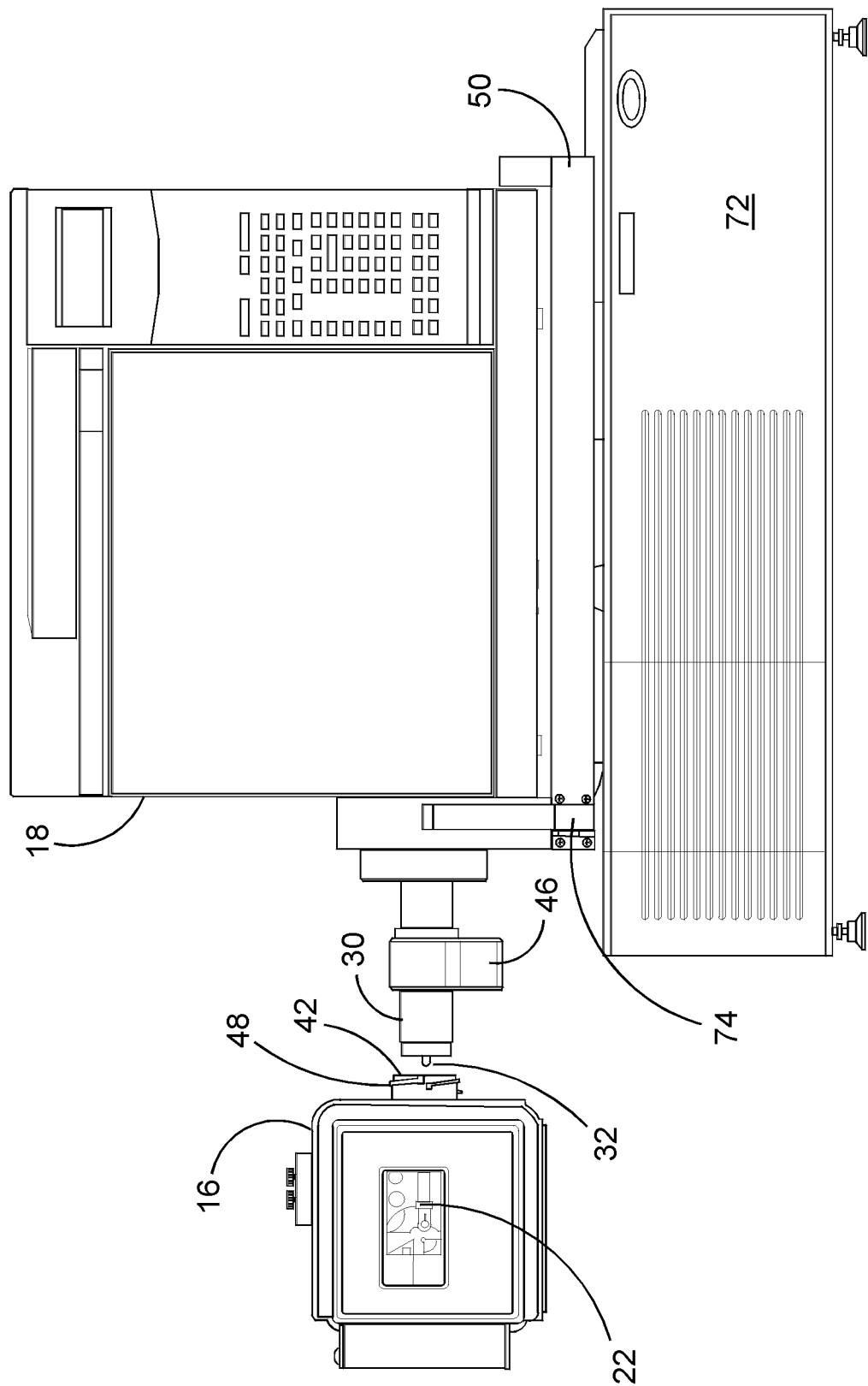
FIG. 4 is a view similar to FIG. 3 but showing the GC interface probe offered up to the GC ion source housing.

Referring to FIGS. 2, 3 and 4, the GC ion source housing 16 includes a nozzle 42 which forms part of complementary docking means for detachably receiving the GC interface probe 30 which incorporates the GC column 32. The nozzle includes a sealing O-ring 44 (FIG. 2) by which the GC interface probe is sealingly engaged in the nozzle. Referring back to FIGS. 3 and 4, the GC interface probe 30 has another part of the complementary docking means which includes a rotatable screw-threaded locking lever 46 which co-operates with a mating screw-threaded portion 48 of the docking nozzle such that when the probe is offered up to the nozzle, engagement of the complementary screw-threaded parts by manipulation of the locking level causes the probe, and hence the GC column, to be progressively docked in the chamber 22 of the GC ion source housing 16.

Figure 5:
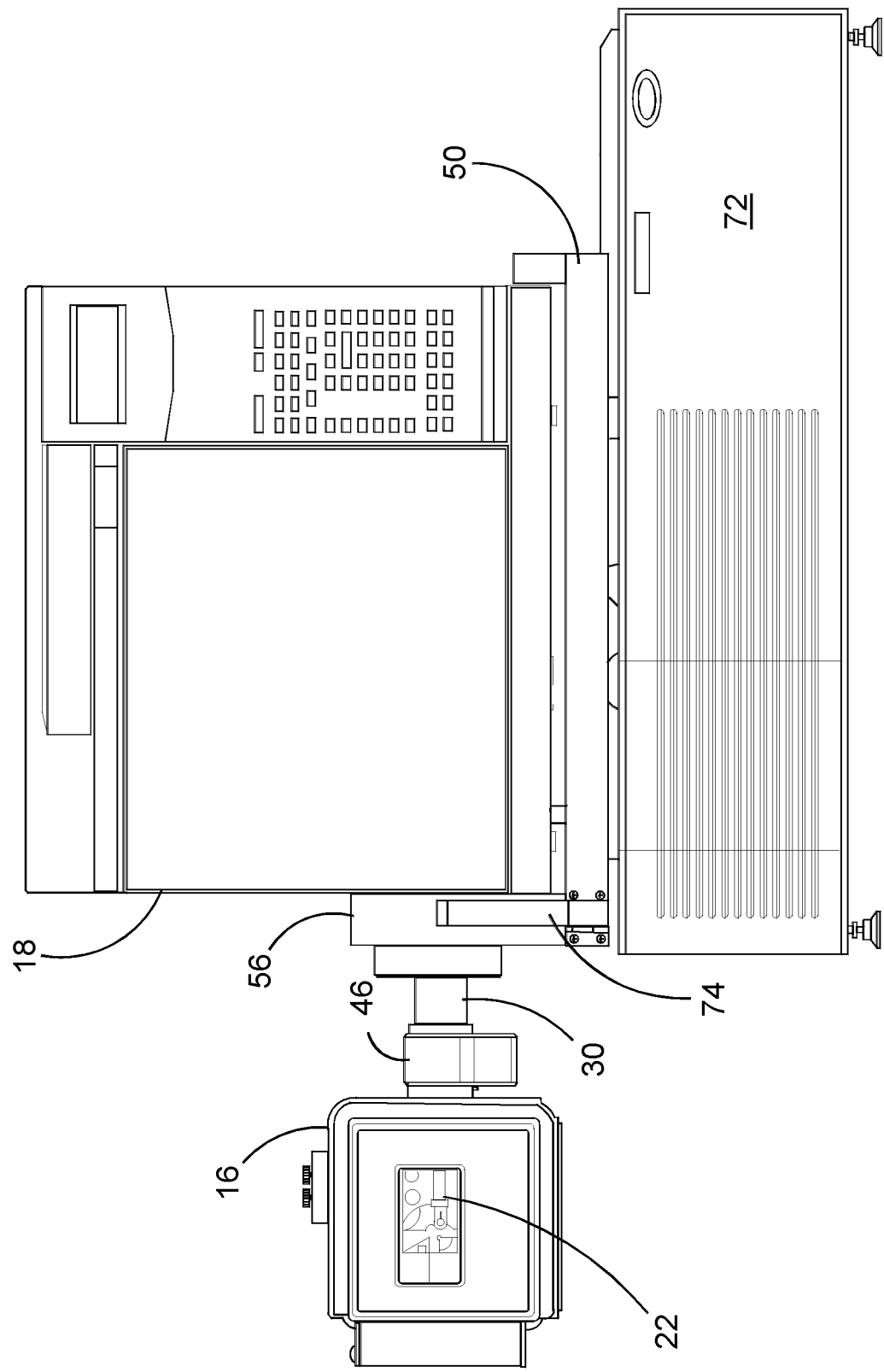
FIG. 5 is a view similar to FIG. 4 but showing the GC interface probe engaged with the GC ion source housing in a deployed position.

In order to take the GC interface probe 30 from a retracted position in which it is disengaged from the GC ion source chamber, whereby the system is operable in a first LC/MS mode, into a deployed position in which the GC interface probe 30 is operatively connected to the GC ion source chamber, whereby the system is operable in a second GC/MS mode, as shown in FIG. 5, the GC unit is slidably mounted on a rail system.

Figure 6:
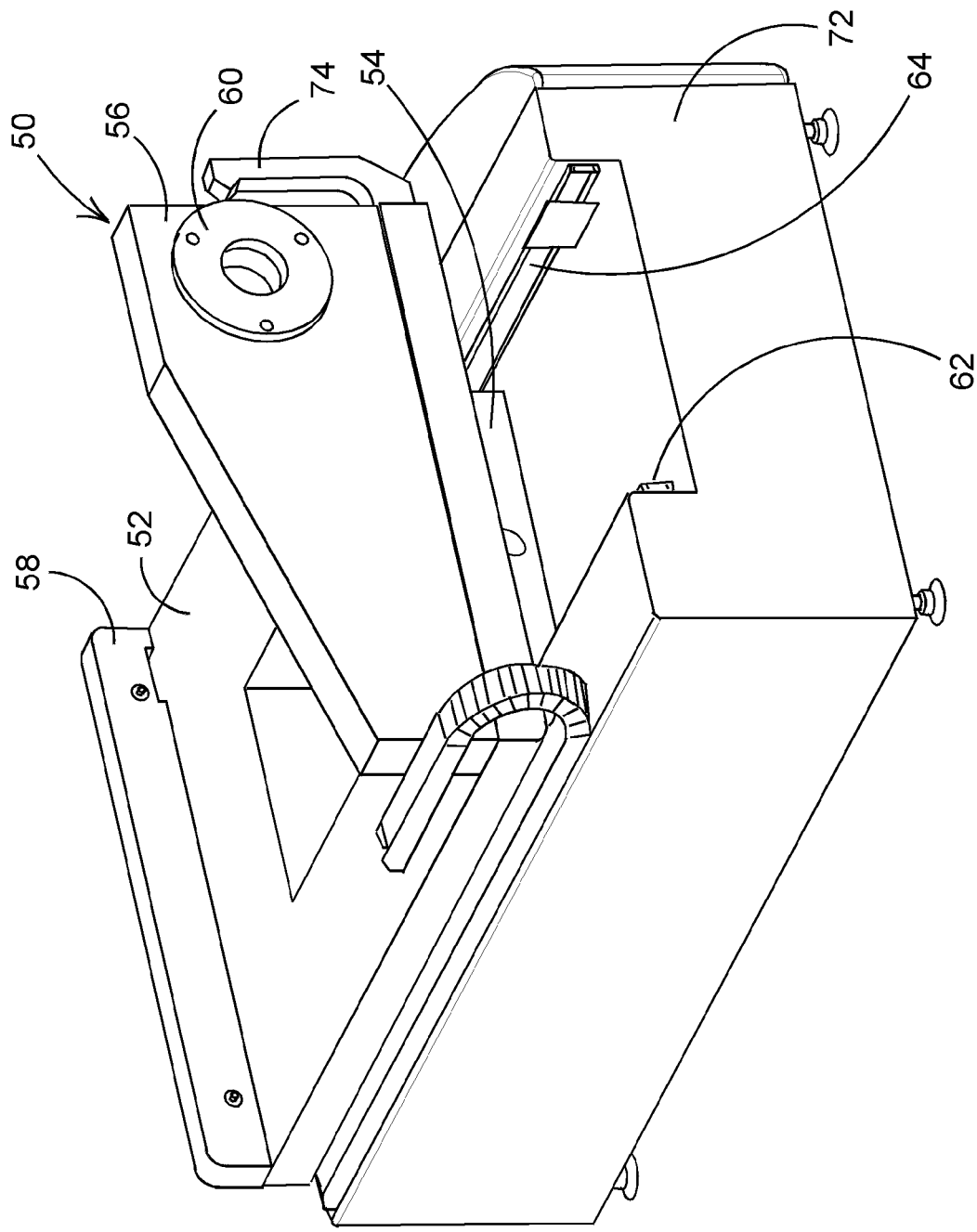
FIG. 6 is a perspective view of a slidable carriage which receives the GC unit and is mounted on rails to a base unit.
Figure 7:
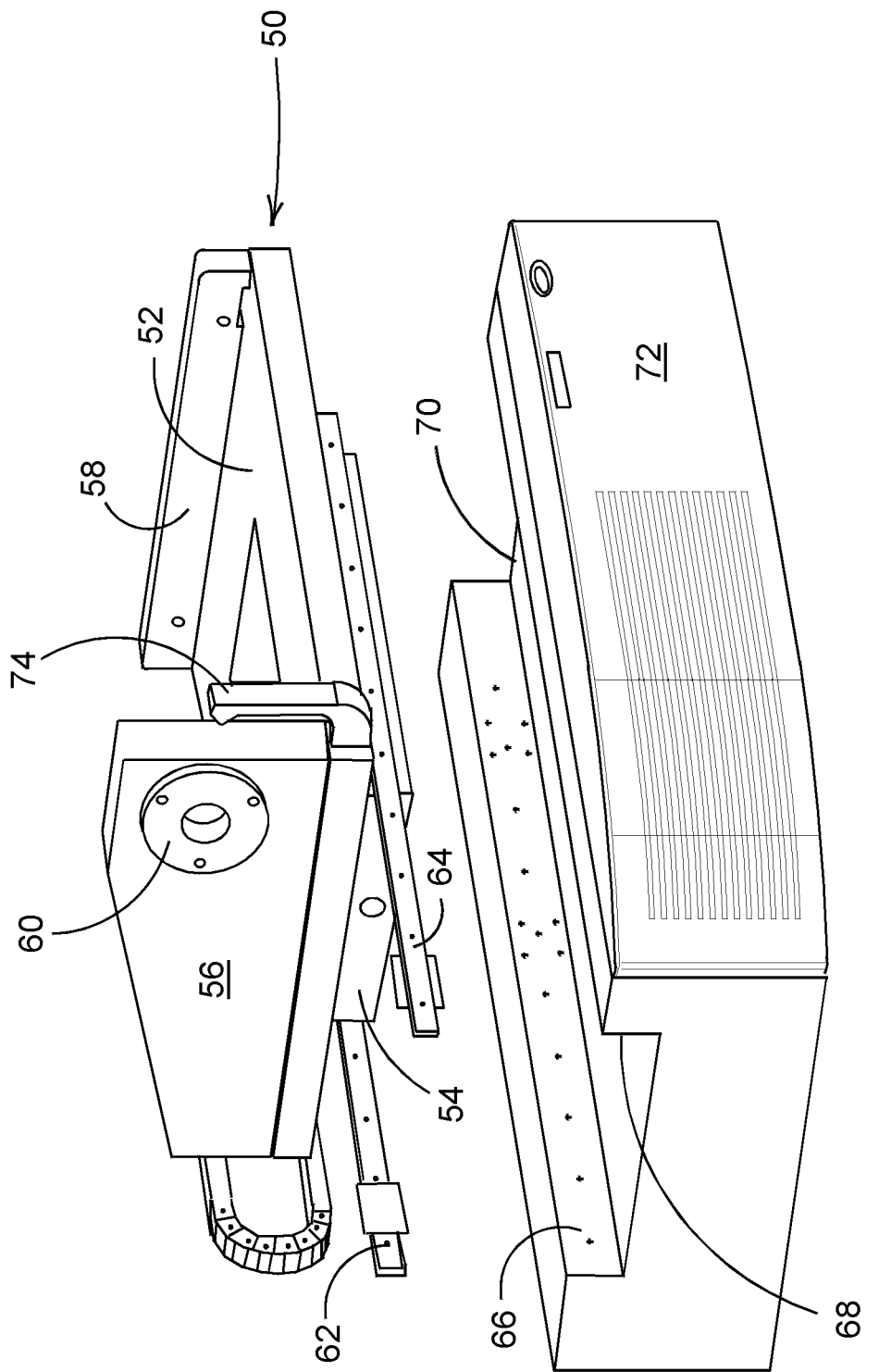
FIG. 7 is an exploded perspective view of the carriage, rail system and base unit.

Referring now to FIGS. 6 and 7 of the drawings, details of the GC unit rail system are shown. The GC unit 18 (see FIGS. 1 to 5) is received in a carriage 50 which includes a floor 52 having a keel portion 54 and end walls 56, 58 respectively by which the GC unit 18 is secured to the carriage 50. End wall 56 includes an opening 60 through which the GC interface probe extends from the GC unit. The keel portion 54 is furnished with a pair of parallel rails 62, 64 (which operate in a manner similar to those found in office filing cabinets) which have runners fixed to opposed walls 66, 68 of a channel 70 formed in the upper face of a base unit 72 so that the keel portion sits with clearance in the channel. Thus the carriage (together with the GC unit 18) can slide to and fro with respect to the base unit. A locking handle 74 is provided by the carriage to assist in the sliding movement of the carriage but also for manipulation to lock the rail 66 against the channel to prevent movement of the carriage relative to the base unit.

The travel of the carriage relative to the base unit is such that when the GC unit is retracted, the GC transfer probe is drawn clear of the MS unit and, at the extremity of its travel in the opposite direction, the GC transfer probe is presented to the docking nozzle so that the complementary docking means can progressively draw in the probe and hence the GC column for operative connection to the chamber.

The invention claimed is:

1. A method of operating a dual source mass spectrometer system in a first mode with an LC source [LC/MS] and in a second mode with a GC source [GC/MS], said GC source inputting into an ion source chamber for delivering the ionized output from the GC source to the mass spectrometer and wherein the GC source comprises a GC interface probe, the method comprising the steps of taking the GC interface probe from a retracted position in which it is disengaged from the ion source chamber, whereby the system is operable in said first LC/MS mode, into a deployed position in which the GC interface probe is operatively connected to the ion source chamber whereby the system is operable in said second GC/MS mode.

2. A method according to claim 1, further comprising actuating complementary docking means provided between the GC interface probe and a housing of the ion source chamber so that they can be releasably engaged to allow operation with a GC ion source chamber in said second mode and substitution of the GC ion source housing by an LC ion source housing to allow operation with the LC ion source chamber in said first mode.

3. A method according to claim 2, wherein the docking means comprises a docking port and the complementary locking means is actuated such that the probe is progressively drawn into the docking port and releasably locked in position.

4. A method according to claim 3, wherein the docking port comprises a screw-threaded nozzle incorporating sealing means and the GC interface probe comprises a complementary screw-threaded locking lever and wherein the locking lever is manipulated to releasably engage the nozzle whereby the probe can be sealingly coupled with the nozzle.

5. A method according to any of claims 1 to 4, wherein the GC interface probe is carried by a gas chromatography unit, and wherein the gas chromatography unit is retractably connected to a mass spectrometer of the system when a GC ion source chamber is present.

6. A method according to claim 5, wherein the gas chromatography unit is slidably connected to the mass spectrometer of the system.

7. A method according to claim 6, wherein the gas chromatography unit incorporates a lockable rail system the method comprising slidable movement of the unit over the rail system so that it is offered up to and retracted from the mass spectrometer of the system.

* * * * *